United States Patent [19]
Gainer

[11] 4,079,253
[45] Mar. 14, 1978

[54] BACK REFLECTION GONIOMETER

[75] Inventor: Michael K. Gainer, Aberdeen, Md.

[73] Assignee: The United States of America as represented by the Secretary of the Army, Washington, D.C.

[21] Appl. No.: 206,548

[22] Filed: Jun. 27, 1962

[51] Int. Cl.² .............................................. G01N 23/20
[52] U.S. Cl. ..................................... 250/273; 250/274
[58] Field of Search ................ 250/51.5, 52, 273, 274, 250/277 R, 277 CH, 279

[56] References Cited

U.S. PATENT DOCUMENTS

| | | | |
|---|---|---|---|
| 2,079,900 | 5/1937 | Cohn | 250/273 |
| 2,386,785 | 10/1945 | Friedman | 250/273 |
| 2,430,969 | 11/1947 | Young | 250/279 |
| 2,500,948 | 3/1950 | Kaiser et al. | 250/279 |
| 2,648,011 | 8/1953 | Good | 250/279 |
| 2,819,405 | 1/1958 | Bond | 250/274 |

FOREIGN PATENT DOCUMENTS 684,282  11/1939  Germany .............................. 250/272

*Primary Examiner*—S. C. Buczinski
*Attorney, Agent, or Firm*—Nathan Edelberg; Robert P. Gibson

EXEMPLARY CLAIM

1. A device for determining preferred crystal orientation in a rotary extruded shaped charge liner used in the field of ballistics comprising: an automatically controlled three circle goniometer type specimen mount; means for emitting a continuous x-ray beam onto a liner mounted in said specimen mount whereby continuous diffraction beams are reflected back in the shape of a cone; continuous detecting means and means to rotate same at the base of said cone; said detecting means being capable of producing electrical signals indicative of the intensity of the diffraction reflected beams; slip ring means connected to said detecting means; and continuous recording means connected to said slip ring means, said recording means providing an indication of the crystal orientation in said liner.

3 Claims, 5 Drawing Figures

INVENTOR.
Michael K. Gainer

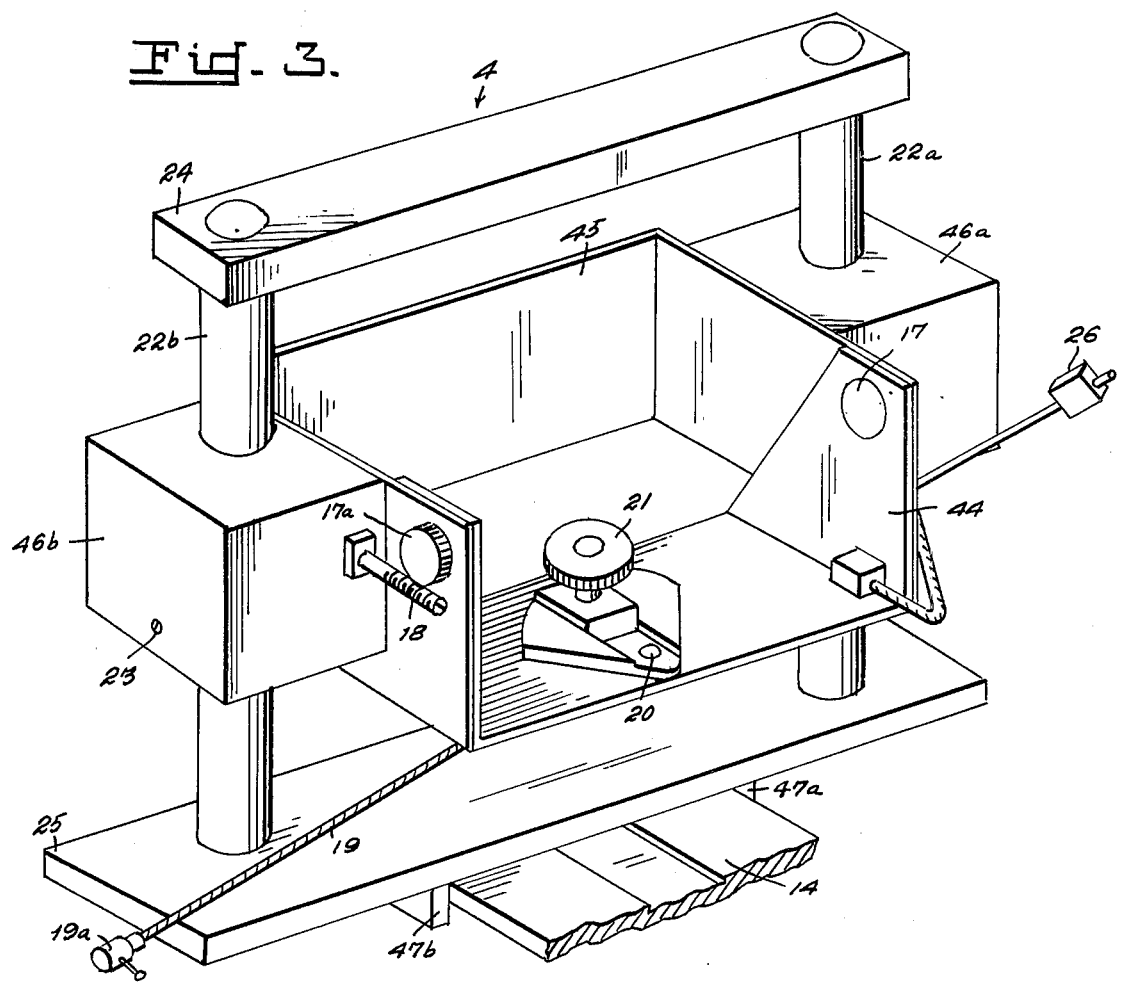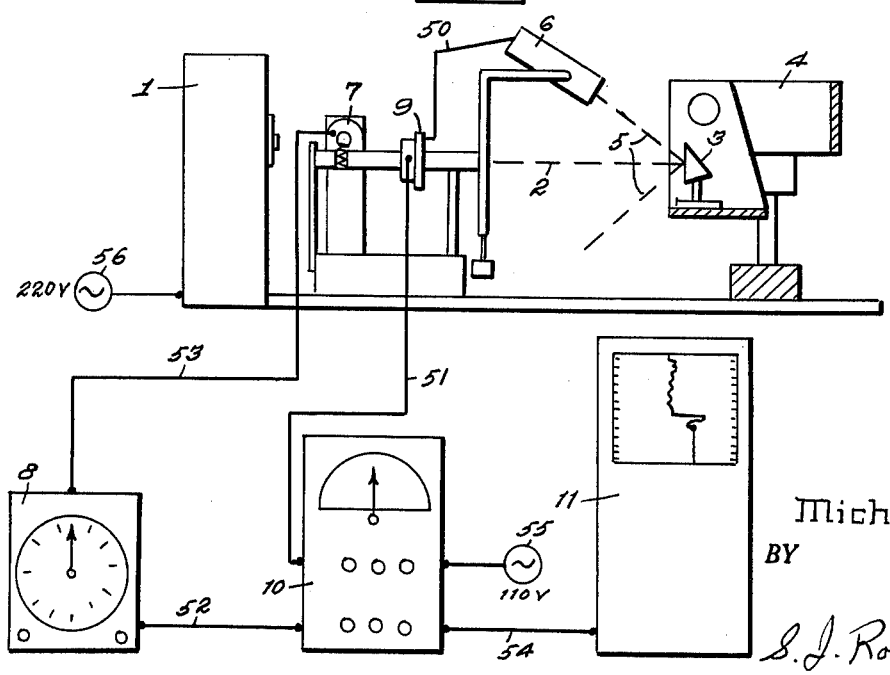

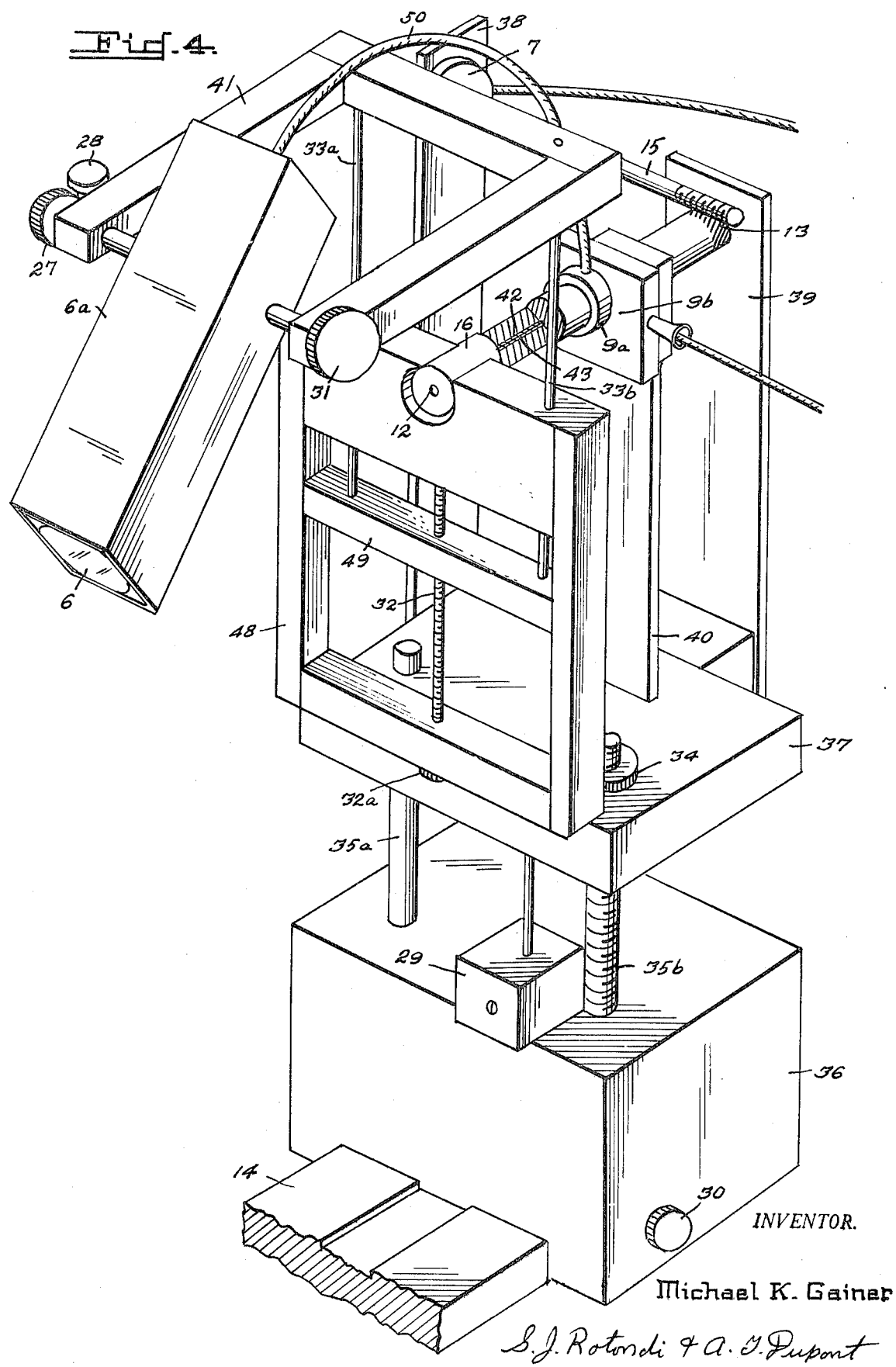

BACK REFLECTION GONIOMETER

The invention described herein may be manufactured and used by or for the Government for governmental purposes without the payment to me of any royalty thereon.

This invention relates generally to metallographic inspection and more particularly to a device and method for making precise quantitative x-ray diffraction analyses of preferred crystal orientation as found in rotary extruded metal liners employed in shaped charge projectiles.

More specifically my invention relates to apparatus for obtaining data usuable in determining the frequency of spin compensation exhibited by a conical shaped charge liner made by the rotary extrusion process.

Spin compensation is the ability of a shaped charge to compensate for an external rotation applied to it, thus allowing the jet formed by the liner to be normal and unaffected by the external rotation. This would seem to indicate that during collapse the liner elements are given a rotation equal and opposite in magnitude to the rotation applied to the system.

General use has been with rounds that have been fin-stabilized, but still many requirements exist for spin-stabilized projectiles having rotational frequencies up to two thousand revolutions per second. Under rotation, a jet from a normal shaped charge liner bifurcates, or breaks up into parallel ribbons. It is generally known that a decrease in penetration is directly related to such bifurcation of the jet.

The most common method of producing a spin compensating round involves a process known as rotary extrusion, which is a modificaton of the standard metal-spinning technique that reorients the crystalline structure. A round metal blank, slightly cupped in the center, is held firmly in place against a rotating mandrel. A circular, friction-driven carboloy tool moves in against the metal blank and travels down the side of the mandrel, maintaining a preset distance between the mandrel and tool edge. The pressure exerted by the tool forces the metal blank to assume the conical shape of the mandrel and with a thickness equal to the preset distance. Once the cone is formed, the excess blank material is removed and a complete liner results with "built in" spin compensation.

The gyroscopic phenomena of spin stabilizing projectiles is old and well accepted in the art of ballistics. However, spin stabilization has been discovered to have an undesirable effect on the detonation of shaped charge projectiles. The depth of penetration of a shaped charge projectile is inversely related to its frequency of rotation, as mentioned previously with regards to jet bifurcation. Fluted or rotary extruded liners are used to counter-rotate or spin compensate those shaped charge projectiles which are spin stabilized. The matching of the frequency of spin stabilization of the projectile in which the liner is housed is primarily a problem of determining the frequency of spin compensation of the liner. This is a small problem in the case of fluted liners since the spin compensation can be accurately determined by an inspection of the geometry of the liner. Determining the frequency of spin compensation of a rotary extruded liner, however, has escaped such a simple solution.

The two principal methods of observing spin compensation have been by the use of penetration-rotation studies and flash x-ray studies of the jet at different frequencies. The former method consists of the determination of the frequency of rotation at which a liner achieves maximum penetration. The latter method is based on the theory that the spin compensation frequency may be taken as the rotation frequency at which the jet is least bifurcated. Both of these tests are costly, slow, and of a destructive nature.

Accordingly, it is a primary object of my invention to provide a method to rapidly determine the spin compensation frequency exhibited by shaped charge liners manufactured by the rotary extrusion process.

Another object of the present invention is to provide a rapid method for determining grain textues or orientations of a poly-crystalline metal.

Still another object of this invention is to provide for a simple, inexpensive method of checking shaped charge liners to assure that they are within proper specifications.

A further object is the determination of the spin compensation of a rotary extruded shaped charge liner by a method which is of a non-destructive nature.

A still further object is the rapid determination of the effects of manufacturing parameters on the crystallagraphic structure of any metal product.

The novel features that are considered characteristic of this invention are set forth with particularity in the appended claims. The invention itself, however, both as to organization and method of operation, as well as additional objects and advantages thereof, will best be understood from the following description when read in connection with the accompanying drawing, in which:

FIG. 3 illustrates a perspective view of the three circle goniometer specimen mount;

FIG. 4 illustrates a perspective and cross sectional view of the Geiger-Mueller tube holder showing the tube, drive motor, commutator, and x-ray collimator; and FIG. 5 illustrates a schematic arrangement of the apparatus necessary to effect the invention.

The present invention incorporates back reflection x-ray techniques to determine the presence of a preferred orientation and is an outgrowth of the Bragg relationship which states that:

$$m\lambda = 2\, n\, d \sin \theta \qquad (1)$$

where
$\lambda$ = wave length of the x-rays,
$d$ = spacing between the atomic planes,
$\theta$ = angle of diffraction between the x-ray beam and atomic plane, and
$n$ = an integer, generally 1 in the present invention.

In the above relationship an x-ray beam inpinges on any metal specimen and the beam is diffracted from an atomic plane. The diffracted x-ray beam either passes through the metal specimen or is reflected back from the plane to a suitably placed x-ray film, through which the x-ray beam has passed originally, thus giving a back reflection pattern.

Usually an x-ray beam of a certain wavelength directed at a metal surface will produce a diffraction of that beam for almost every type of atomic plane in the metal. These diffracted beams fan out in the shape of a cone. The shape and location of the base of each cone is a function of the weavelength of the x-ray and the characteristics of the plane causing the diffraction. As mentioned previously, a piece of film placed in the cone of diffraction of a piece of metal with a randomly oriented grain distribution will indicate such distribution by showing a uniform circle. However, a piece of film placed in the diffraction cone of a rotary extruded liner will show definite maximum and minimum areas of intensity in the circle, indicating the presence of a preferred grain orientation.

Figure 1:
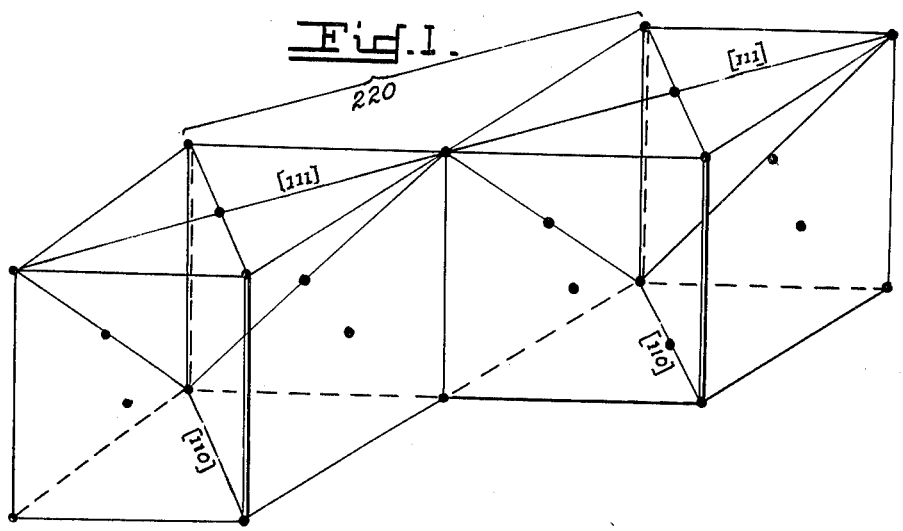
FIG. 1 illustrates a perspective view of two face centered cubes showing the [110], {111}, and [220] planes.

Referring now to the drawing in which like components have been designated by the same reference numerals and particularly to FIG. 1, there is illustrated a perspective view of two face centered cubes. The slip systems of the cubes were found to be in the [110] direction in the {111} plane, or in the closely packed direction in the closely packed plane. To obtain an indication of the presence of a preferred orientation in face centered cubic metals using back reflection x-ray techniques, a second order reflection such as the [220] or {222} is used since the [110] and {111} x-ray reflections are not conveniently located in the back reflection region. The {222} plane is a second order reflection from two {111} planes.

The film exposed to the diffraction cone of the [220] planes in a rotary extruded liner exhibit two predominant areas of intensity in the circle which are approximately 180° apart. In other words, the intensity varies around a given ring with distinct maxima and minima.

Figure 2:
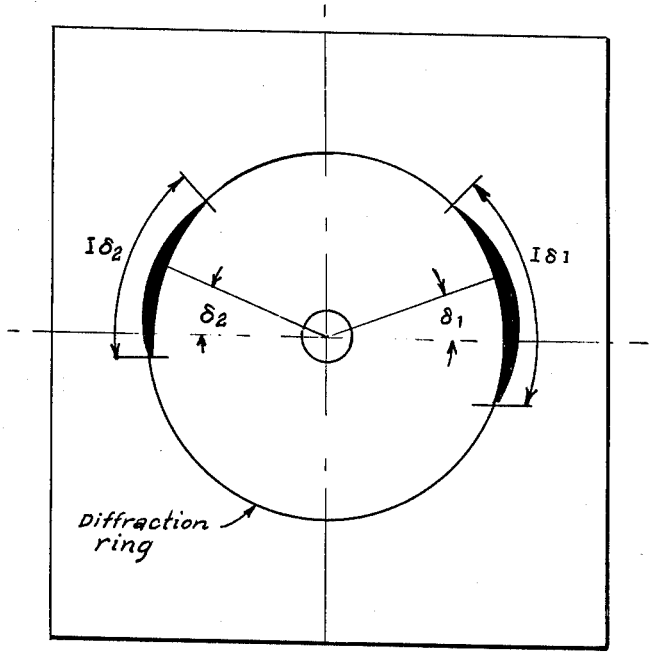
FIG. 2 is an example of a diffraction ring detected and displayed in a quantitative manner by the present invention.

An example of such a diffraction ring can be seen in FIG. 2. The angles $\delta_1$ and $\delta_2$ represent the angles from the horizontal to the points of maximum intensity on either side of the diffraction ring. The intensity spread, which indicate the widths of the region of maximum intensity are identified as $I\delta_1$ and $I\delta_2$ respectively. $I\delta_1 - I\delta_2$ is the difference in intensity of the two intensity maxima observed on the film. This difference of intensity between the areas is indicative of the spin compenstion possessed by a shaped charge liner. Further tests show that a point one inch from the base of the liner at a depth of one-third of the thickness of the liner wall give an accurate determination of the frequency of spin compensation.

Referring to the drawings, the three circle goniometer mount shown in FIG. 3 is generally indicated by 4 and consists of a specimen mount 21 rotatably mounted in a pivotable carriage 44 supported by rearwardly extending portion 45 and blocks 46a and 46b. These blocks are slideably mounted on tubular members 22a and 22b respectively, which are supported by frame 25. Cross member 24 adds rigidity to the structure.

A worm gear (not shown) on the underside of bolt 20, and worm driven by drive shaft 19, provide horizontal angle adjustment means for specimen mount 21. A mechanism 19a is provided for attaching worm drive shaft 19 to a motor and timer to allow the horizontal angle adjustments to be made automatically. Worm 18 and worm gear 17a provide vertical angle adjustment means for carriage 44 about carriage bolts 17.

Set screw 23 provides a locking means for block 46b and a similar set screw is used for block 46a. Counterbalance 26 is provided as a further balancing feature. The entire goniometer asembly is slideably mounted on ramp 14 and held thereon by shoulders 47a and 47b.

The Geiger-Mueller tube rotation assembly is shown in FIG. 4. The Geiger-Mueller tube 6 is integrally secured in holder 6a which is pivotably mounted in u-shaped frame 41. The tube holder 6a is provided with a locking screw 31 for course adjustment and worm 28 with worm wheel 27 for fine adjustment. The u-shaped frame 41 is slideably secured to a lower assembly 48 by rods 33a and 33b. Vertical adjustments of the Geiger-Mueller tube 6 are provided by threaded shaft 32, knob 32a, and bar 49 to which the rods 33a and 33b are attached. A counterbalance 29 may be adjustably mounted on frame 48 to be moved in toward shaft 16 or outwardly in a well-known manner.

The entire rotating porton of the assembly is secured to and rotates with a shaft 16 which is rotatively mounted in support 39 and slip ring elements 9a and 9b. This slip ring provides the means of transferring electrical signals to and from the rotating Geiger-Mueller tube 6. The slip ring is electrically connected to the Geiger-Mueller tube 6 by means of conductor 50 and is integrally fixed to shaft 16. It thus transmits electrical signals to a stationary contact member 9b.

A motor 7, mounted on support 38, drives shaft 16 through a worm 15 and worm gear 13.

Supports 38, 39 and 40 are mounted on plate 37 which is adjustably mounted on base 36 by means of tubular supports 35a and 35b. Plate 37 is secured by threaded support 35b and locking nut 34. Base 36 is slideably mounted on ramp 14 with locking means supplied by locking bolt 30.

A collimator 42 is provided in shaft 16 with a narrow bore 43 for allowing passage of an x-ray beam. Aperture 12 is provided to allow the x-ray beam a passage through the end of shaft 16.

A schematic of the apparatus employed to effect the invention is pictured in FIG. 5. A combination rate meter and power supply 10, of the type manufactured by Nuclear Chicago, supplies power to the Geiger-Mueller tube 6 by means of leads 51, commutator 9 and conductor 50. It also provides the power for synchronous motor 7 through conductor 52, timer 8 and conductor 53.

Power supplies indicated at 55 and 56 provide the 110 and 220 volts necessary for operation of the combination rate meter and power supply 10 to x-ray machine 1, respectively.

The wavelength of the x-rays must be of a value such that the angle of diffraction $\theta$ will neither be too large nor too small. The apparatus shown in FIG. 5 is able to detect those angles of diffraction between 20° and 70°.

In operation, x-ray machine 1 emits a beam 2 toward a specimen 3. The primary beam 2 is diffracted off of specimen 3 and is shown as diffracted beam 5. Geiger-Mueller tube 6, rotating in the cone of diffractred beam 5 detects the varous intensities of diffracted beam 5 in its cone of diffraction. An electrical pulse indicative of the intensity of the beam 5 is transferred through commutator 9 and ratemeter 10 to recorder 11. Ratemeter 10 provides an instantaneous reading of the intensities being received by Geiger-Mueller tube 6.

The recorded intensities of the diffracted beam 5 will show two definite areas of maximum intensity for each rotation of the Geiger-Mueller tube 6. The location of the larger intensity maximum and the difference between the two intensity maxima will provide data usuable in establishing the direction and magnitude of any spin compensation present in a shaped charge liner due to a preferred grain orientation.

It is only necessary to make one revolution of the Geiger-Mueller tube at the aforementioned point one inch above the liner base and one third of the distance through the liner wall to accurately determine the spin compensation. The liner is still usable after a test of this nature is made. It should be mentioned that liners made of any metal can be tested by this method, as well as those having face centered cubes.

In a modificaton of this device, the shaped charge liner can be rotated about the incident beam while holding the Geiger-Mueller beam stationary. The liner is rotated so that the surface is always normal to the beam. This results in a more rugged device and one which is more adaptable to production line inspection.

Although a specific embodiment of this invention has been illustrated and described, it will be understood that this is but illustrative and that various modificatons may be made therein without departing from the scope and spirit of my invention.

What is claimed is:

1. A device for determining preferred crystal orientation in a rotary extruded shaped charge liner used in the field of ballistics comprising: an automatically controlled three circle goniometer type specimen mount; means for emitting a continuous x-ray beam onto a liner mounted in said specimen mount whereby a continuous diffraction beams are reflected back in the shape of a cone; continuous detecting means and means to rotate same at the base of said cone; said detecting means being capable of producing electrical signals indicative of the intensity of the diffraction reflected beams; slip ring means connected to said detecting means; and continuous recording means connected to said slip ring means, said recording means providing an indication of the crystal orientation in said liner.

2. A device as defined in claim 1, further comprising motor means connected to said detecting means for providing rotation thereto.

3. A device as defined in claim 2, further comprising timer means connected to said motor means to control the energization of said motor means so that said detecting means makes one complete revolution around said base of the diffraction cone.

* * * * *